(12) United States Patent
Figge

(10) Patent No.: US 9,267,160 B2
(45) Date of Patent: Feb. 23, 2016

(54) INCREASING METHIONINE PRODUCTION BY OVEREXPRESSING SUCCINATE DEHYDROGENASE

(75) Inventor: Rainer Figge, Le Crest (FR)

(73) Assignee: METABOLIC EXPLORER, Saint Beauzire (FR)

( * ) Notice: Subject to any disclaimer, the term of this patent is extended or adjusted under 35 U.S.C. 154(b) by 575 days.

(21) Appl. No.: 13/519,507

(22) PCT Filed: Dec. 30, 2009

(86) PCT No.: PCT/IB2009/056063
§ 371 (c)(1),
(2), (4) Date: Jul. 19, 2012

(87) PCT Pub. No.: WO2011/080542
PCT Pub. Date: Jul. 7, 2011

(65) Prior Publication Data
US 2012/0288903 A1    Nov. 15, 2012

(51) Int. Cl.
*C12P 13/12*    (2006.01)

(52) U.S. Cl.
CPC ....................................... *C12P 13/12* (2013.01)

(58) Field of Classification Search
None
See application file for complete search history.

(56) References Cited

U.S. PATENT DOCUMENTS

| | | | |
|---|---|---|---|
| 7,745,195 B2 | 6/2010 | Chateau et al. | |
| 7,785,846 B2 | 8/2010 | Boy et al. | |

FOREIGN PATENT DOCUMENTS

| | | | |
|---|---|---|---|
| EP | 1 106 684 | | 6/2001 |
| JP | 2000157267 | | 6/2000 |
| WO | 03/008607 | | 1/2003 |
| WO | 2004/076659 | | 9/2004 |
| WO | 2005/007862 | | 1/2005 |
| WO | 2005/059155 | | 6/2005 |
| WO | 2005/111202 | | 11/2005 |
| WO | WO 2007/011939 | * | 1/2007 |
| WO | 2007/017710 | | 2/2007 |
| WO | 2007/020295 | | 2/2007 |
| WO | 2007/077041 | | 7/2007 |
| WO | 2009/043803 | | 4/2009 |
| WO | 2009/078973 | | 6/2009 |
| WO | 2009/133063 | | 11/2009 |

OTHER PUBLICATIONS

Tornroth et al., Purification, crystallisation and preliminary crystallographic studies of succinate:ubiquinone oxidoreductase from *Escherichia coli*., Biochimica et Biophysica Acta (2002), vol. 1553, Issues 1-2, pp. 171-176.*
S5XHZ5 (last viewed on Dec. 31, 2014).*
S5XHZ6 (last viewed on Dec. 31, 2014).*
S5XZM3(last viewed on Dec. 31, 2014).*
International Search Report Based on Application No. PCT/IB2009/056063 Mailed Oct. 12, 2010.
Brosius et al.; "Spacing of the -10 and -35 Regions in the TAC Promoter"; The Journal of Biological Chemistry; Issue of Mar. 25, 1985; vol. 260; No. 6; pp. 3539-3541; The American Society of Biological Chemists, Inc.
Bussmann et al.; "Transcriptional Control of the Succinate Dehydrogenase Operon SDHCAB of Corynebacterium Glutamicum by the CAMP-Dependent Regulator GlXR and the LUXR-Type Regulator RAMA"; Journal of Biotechnology 143; 2009; pp. 173-182; Elsevier B.V.
Cheng et al.; "Alternative Sites for Proton Entry From the Cytoplasm to the Quinone Binding Site in *Escherichia coli* Succinate Dehydrogenase"; Biochemistry; vol. 47; 2008; pp. 9107-9116; American Chemical Society.
De Boer et al.; "The TAC Promoter: A Functional Hybrid Derived From the TRP and LAC Promoters"; Proc. Natl. Acad. Sci; Jan. 1983; vol. 80; pp. 21-25.
Dickson et al.; "Genetic Regulation: The LAC Control Region"; 1975; vol. 187 (4171); pp. 27-35.
Orosz et al.; "Analysis of the Complex Transcription Termination Region of the *Escherichia coli* RRNB Gene"; Eur. J. Biochem.; 1991; vol. 201; pp. 653-659; FEBS.
Figge; "Methionine Biosynthesis in *Escherichia coli* and Corynebacterium Glutamicum"; Microbiol Monogr 5; 2007; vol. 5; pp. 163-193; Springer-Verlag Berlin Heidelberg.
Yankovskaya et al.; "Architecture of Succinate Dehydrogenase and Reactive Oxygen Species Generation"; Science; Jan. 31, 2003; vol. 299.
Carrier et al.; "Biotechnology Progress"; 1999; vol. 15; No. 1; pp. 58-64.

* cited by examiner

*Primary Examiner* — Alexander Kim
(74) *Attorney, Agent, or Firm* — Miles and Stockbridge

(57) ABSTRACT

The present invention relates to a process for improving the production of methionine by culturing a microorganism modified for enhancing the expression of genes involved in succinate dehydrogenase synthesis. The microorganisms were modified in a way that the methionine/carbon source yield is increased. The isolation of methionine from the fermentation medium is also claimed.

9 Claims, No Drawings

INCREASING METHIONINE PRODUCTION BY OVEREXPRESSING SUCCINATE DEHYDROGENASE

CROSS REFERENCE TO RELATED APPLICATIONS

This application is a §371 National Stage Application of PCT/EP2009/056063, filed Dec. 30, 2009.

BACKGROUND OF THE INVENTION

1. Field of the Invention

The present invention relates to a process for improving the production of methionine by culturing a microorganism modified for enhancing the expression of genes involved in succinate dehydrogenase synthesis. The microorganisms were modified in a way that the methionine/carbon source yield is increased. The isolation of methionine from the fermentation medium is also claimed.

2. Description of Related Art

Succinate dehydrogenase (succinate oxidoreductase, SQR) is a functional member of both the Krebs cycle and the aerobic respiratory chain. SQR catalyzes the oxidation of succinate to fumarate in the bacterial cytoplasm with the concomitant reduction of ubiquinone in the membrane. In *E. coli* and other bacteria the enzyme is comprised of four subunits. The two hydrophobic subunits, SdhC and SdhD, anchor two hydrophilic and catalytic subunits SdhA and SdhB to the surface of the inner membrane. Five unique cofactors are involved in the oxidation of succinate to fumarate. In SdhA a covalently attached flavin adenine dinucleotide (FAD) molecule is present to catalyze succinate oxidation by a hydride transfer mechanisms. Electrons are then transferred individually through the electron transfer subunit (SdhB) which contains a [2Fe-2S], a [4Fe-4S] and a [3Fe-4S] cluster. A quinone binding site is formed by residues from SdhC, SdhD and SdhB permitting the reduction of ubiquinone to ubiquinole. The enzyme contains also a heme b molecule sandwiched between SdhC and SdhD that is not essential to enzyme function (Yankovskaya et al. 2003, Science 299, 700; Cheng et al. 2008 Biochemistry 47, 6107).

The amino acid L-methionine is an important feed-additive that is produced in large quantities (600000 t/an). Production relies exclusively on chemical biosynthesis and requires crude oil derived precursors. With increasing pressure on the price of these non-renewable resources a sustainable process receives increasing interest. Fermentative production of methionine has thus become an economically viable alternative to the chemical process.

Methionine production by fermentation requires modification of several precursor-providing pathways. Three majors routes contribute to methionine biosynthesis. Aspartate serves as the precursor of the carbon skeleton, cysteine as sulphur donor and methylene-THF as donor of the terminal methyl group. In addition, activation of aspartate-derived homoserine by succinyl-CoA is required for the first step in methionine biosynthesis. Succinyl-CoA is produced in the Krebs cycle and thus increased expression of Krebs cycle enzymes may increase methionine production. Nevertheless high Krebs cycle activity has been shown to be a disadvantage to amino acid production and reducing the activity of Krebs cycle enzymes, such as isocitrate dehydrogenase, can be beneficial to amino acid production (WO2007017710 Metabolic Explorer, WO2009133063 Evonik Industries).

WO 2009078973 (Glycos Biotechnology) and EP1106684 (Evonik Industries) disclose that the deletion of sdh genes, increases the production of amino acids and other metabolites of industrial interest. It is understood from this art that decreasing expression of sdh genes will lower Krebs cycle activity and thus $CO_2$ production, which in turn should have a positive impact on product yield.

There is a need to increase the yield of methionine being produced form a renewable carbon source. Contrary to the teaching of the prior art, that decreased activity of the succinate dehydrogenase increases product yield, it was found that increased expression of the succinate dehydrogenase enzyme increases methionine/glucose yield.

SUMMARY

The invention relates to a method for increasing the production of methionine, in a fermentative process comprising the steps of culturing a microorganism modified for an improved production of methionine in an appropriate culture medium comprising a source of carbon and a source of sulfur, and of recovering methionine from the culture medium, wherein the microorganism is further modified by enhancing expression of gene(s) coding for a succinate dehydrogenase (sdh) enzyme.

Expression of this (these) gene(s) is enhanced by inserting into the microorganism at least one supplementary copy of said gene(s) coding for succinate dehydrogenase.

In another embodiment of the invention the methionine is further isolated from the culture medium.

The invention also relates to a microorganism, preferentially enterobacteriaceae, coryneform bacteria, yeast, or fungus which is optimized for the production of methionine by overexpressing the succinate dehydrogenase. This microorganism used in the process of the invention allows an increased methionine/carbon source yield increased.

DETAILED DESCRIPTION OF A PREFERRED EMBODIMENT

Microorganism Producing Methionine

The invention is related to a method for production of methionine in a fermentative process by culturing a modified microorganism. According to the invention the terms "culture", 'fermentation' or 'fermentative process" are used interchangeably to denote the growth of bacteria on an appropriate growth medium containing a simple carbon source. This simple carbon source is metabolised by the microorganism for producing methionine.

Another object of the invention is a modified microorganism for use in such a method for the production of methionine in a fermentative process. According to the invention, the term "microorganism" designates a bacterium, yeast or fungus. Preferentially, the bacterium is selected among Enterobacteriaceae, Corynebacteriaceae. More preferentially, the microorganism is a species of *Escherichia*, *Klebsiella*, *Pantoea*, *Salmonella* or *Corynebacterium*. In the most preferred embodiment the bacterium is selected among the group of *Escherichia coli* and *Corynebacterium glutamicum*.

The microorganisms of the invention preferably comprise endogenous gene(s) coding for a sdh enzyme.

The term "microorganism modified for an improved production of methionine" denotes a microorganism that has been genetically modified for improving the production of methionine by metabolising a simple carbon source in comparison with the microorganism non-modified. Such modifications may correspond to enhanced, modulated or decreased expression of genes involved in the methionine biosynthesis pathway. The man skilled in the art knows how to modulate the expression of specific genes. Usual modifications include transforming microorganisms with genetic elements, including gene replacements, modification of promoters, and introduction of vectors for the expression of heterologous or endogenous genes.

The modified microorganism according to the invention is modified by enhancing the expression of at least one gene coding for one of the subunits of the succinate dehydrogenase enzyme. Preferably all genes coding for the different subunits of the succinate dehydrogenase enzyme are overexpressed. The succinate dehydrogenase is generally an enzyme complex containing at least three subunits. Each subunit is encoded by one gene. For example, *Corynebacterium* species contain three genes sdhA, sdhB and sdhC encoding the succinate dehydrogenase (Bussmann et al., 2009, J. Biotechnol, 143(3), 173) whereas other microorganisms such as *E. coli* or *S. cerevisiae* have four genes for four succinate dehydrogenase subunits. These sdh genes are organized in operon. The term operon describes a unit of transcription wherein several genes are transcribed in a polycistronic messenger RNA. (*E. coli* accession numbers for sdhA: P0AC41, sdhB: P07014, sdhC: P69054, sdhD P0AC44).

The terms "enhancing' or 'enhanced' or 'overexpressed' or 'increased expression' 'enhanced expression' or 'overexpression" are used interchangeably in the text and have similar meaning. These terms, in this context, describe the increase in the intracellular activity of an enzymatic activity which is encoded by the corresponding DNA, for example by increasing the number of copies of the gene, using a stronger promoter or using an allele with increased activity and possibly combining these measures. These promoters may be inducible; they may be homologous or heterologous. The man skilled in the art knows which promoters are the most convenient, for example promoters Ptrc, Ptac, Plac (Dickson et al., 1975, Science 187(4171), 27; de Boer et al., 1983, Proc Natl Acad Sci USA, 80(1), 21; Brosius et al., 1985, J Biol Chem, 260(6), 3539) or the lambda promoter cI (Ptashne M, 1986, Blackwell Scientific, Cambridge, Mass.; Ptashne M, 2004, Cold Spring Harbor Lab Press; Little J, 2004, Richard Calendar.ed. Oxford University Press) are widely used.

When genes are organized in an operon, it is possible to enhance their expression by adding one supplementary copy of these genes under control of a single promoter. Expression may also be enhanced by replacing the chromosomal wild-type promoter with an artificial promoter stronger than the wild-type promoter. The expert in the field knows how to determine promoter strength.

To increase the expression of a gene it may be encoded chromosomally or extrachromosomally. Copies of genes may be added chromosomally or extrachromosomally. Chromosomally there may be one or several extra copies on the genome that may be introduced by methods of recombination known to the man skilled in the art. Extrachromosomally genes may be carried by different types of plasmids or Bacterial Artificial Chromosomes that differ with respect to their origin of replication and thus their copy number in the cell. They may be present as 1-5 copies, about 20 or up to 500 copies, corresponding to low copy number plasmids with tight replication (e.g. pSC101, RK2), low copy number plasmids (e.g. pACYC, pRSF1010) or high copy number plasmids (e.g. pSK bluescript II). In a preferred embodiment of the invention, sdh genes may be overexpressed using extrachromosomal expression. In this embodiment of the invention sdh genes are carried by a Bacterial Artificial Chromosome.

Expression of the enzymes may be boosted or reduced by elements stabilizing or destabilizing the corresponding messenger RNA (Carrier and Keasling, 1998, Biotechnol. Prog. 15, 58) or the proteins (e.g. GST tags, Amersham Biosciences).

The microorganisms, according to the present invention, contain one or several alleles of the genes to be enhanced according to the invention. Preferably the microorganism, according to the invention, is carrying one supplementary copy of genes coding for the succinate dehydrogenase enzyme. In a preferred embodiment of the invention, these genes are cloning in the Bacterial Artificial Chromosome pCC1BAC.

In another embodiment of the invention, the microorganism contains one supplementary copy of the four genes sdhA, sdhB, sdhC and sdhD of *E. coli*. Genes in said supplementary copy may be organized in an operon. In a particular embodiment of the invention, the microorganism comprises at least one additional copy of the genes encoding the succinate dehydrogenase of *E. coli*.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models; www dot sanger dot ac dot uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; www dot ncbi dot nlm dot nih dot gov/COG/) are obtained by comparing protein sequences from 66 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website www dot ncbi dot nlm dot nih dot gov/BLAST/ with the default parameters indicated on that website. The sequences obtained can then be exploited (e.g., aligned) using, for example, the programs CLUSTALW (www dot ebi dot ac dot uk/clustalw/) or MULTALIN (prodes dot toulouse dot inra dot fr/multalin/cgi-bin/multalin.pl), with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. $2^{nd}$ ed. Cold Spring Harbor Lab., Cold Spring Harbor, N.Y.).

The modified microorganism according to the invention may further comprise other modifications to enhance methionine production. Preferably, the microorganism of the invention comprises in addition to an enhanced expression of gene(s) coding for a sdh enzyme, additional modifications to enhance methionine production. Modifications for increasing the methionine production are well known in the art. These modifications are for example described in WO2009/043803, WO2007/077041, WO2005/111202, which are incorporated herein by reference. For improving the production of methionine, the microorganism may exhibit an increased expression of at least one gene selected in the group consisting of:

cysP which encodes a periplasmic sulphate binding protein, as described in WO2009/043803 and in, cysU which encodes a component of sulphate ABC transporter, as described in WO2009/043803, cysW which encodes a membrane bound sulphate transport protein, as described in WO2009/043803, cysA which encodes a sulphate permease, as described in WO2009/043803, cysM which encodes an O-acetyl serine sulfhydralase, as described in WO2009/043803, cysI and cysJ encoded respectively the alpha and beta subunits of a sulfite reductase as described in WO2009/043803. Preferably cysI and cysJ are together overexpressed, cysI which encodes a sulfite reductase, alpha subunit, as described in WO2009/043803, cysH which encodes an adenylylsulfate reductase, as described in WO2009/043803, cysE which encodes a serine acyltransferase, as described in WO2007/077041, gcvT which encodes a tetrahydrofolate dependent aminomethyl transferase, as described in WO2009/043803, gcvH which is involved in glycine cleavage by encoding a carrier of aminoethyl group, as described in WO2009/043803, gcvP which encodes a glycine dehydrogenase, as described in WO2009/043803, lpd which encodes a lipoamide dehydrogenase, as described in WO2009/043803, serA which encodes a phosphoglycerate dehydrogenase, as described in patent application WO2009/043803, serB which encodes a phosphoserine phosphatase, as described in patent application WO2009/043803, serC which encodes a phosphoserine aminotransferase, as described in patent application WO2009/043803, glyA which encodes a serine hydroxymethyltransferase, as described in WO2009/043803, metF which encodes a 5,10-methylenetetrahydrofolate reductase, as described in WO2007/077041, metA alleles which encode an homoserine succinyltransferases with reduced feed-back sensitivity to S-adenosylmethionine and/or mathionine as described in WO2005/111202, thrA or thrA alleles which encode aspartokinases/homoserine dehydrogenase with reduced feed-back inhibition to threonine, as described in WO2009/043803, metH which encodes a B12-dependent homocysteine-N5-methyltatrahydrofolate transmethylase as described in WO2007/077041.

In another embodiment of the invention, the microorganism may exhibit an inhibition of the expression of at least one of the following genes:

pykA which encodes a pyruvate kinase, as described in WO2009/043803, pykF which encodes a pyruvate kinase, as described in WO2009/043803, purU which encodes a formyltetrahydrofolate deformylase, as described in WO2009/043803, metJ which encodes the methionine repressor as described in JP 2000/157267.

In another embodiment of the invention the following modified genes encoding enzymes with modified feed-back inhibition properties may be used:

metA mutants encoding enzymes with reduced feed-back sensitivity to methionine and S-adenosylmethionine as described in WO2005108561 thrA mutants with reduced feed-back sensitivity to threonine as described in WO2005108561.

Microorganisms, according to the present invention, may be further modified for increasing production of methionine by using an altered metB allele that uses preferentially or exclusively H2S for the production of homocysteine from O-succinyl-homoserine as described in the patent application WO2004/076659 that is herein incorporated by reference.

All patents and patent applications disclosed above related to methionine production are incorporated herein by reference.

The terms attenuated expression, repressed expression or attenuation, inhibition are used interchangeably in the text and have similar meaning. In this context, the term denotes the partial or complete suppression of the expression of a gene, which is then said to be "attenuated". This suppression of expression can be either an inhibition of the expression of the gene, a deletion of all or part of the promoter region necessary for the gene expression, a deletion in the coding region of the gene, or the exchange of the wildtype promoter by a weaker natural or synthetic promoter. Preferentially, the attenuation of a gene is essentially the complete deletion of that gene, which can be replaced by a selection marker gene that facilitates the identification, isolation and purification of the strains.

In a specific embodiment of the invention, the modified microorganism overexpresses at least one gene selected in the group consisting in cysP, cysU, cysW, cysA, cysM, cysJ, cysI, cysH, cysE, gcvT, gcvH, gcvP, lpd, serA, serB, serC, glyA, metF, metA (with reduced feed-back sensitivity), thrA and metH.

In another embodiment of the invention, the modified microorganism has an attenuated expression of at least one gene selected in the group consisting in pykA, pykF, metJ and purU.

In another embodiment of the invention, the modified microorganism overexpresses at least one gene selected in the group consisting in cysP, cysU, cysW, cysA, cysM, cysJ, cysI, cysH, cysE, gcvT, gcvH, gcvP, lpd, serA, serB, serC, glyA, metF, metA (with reduced feed-back sensitivity), thrA (preferentially with reduced feed-back sensitivity) and metH and represses at least one gene selected in the group consisting in pykA, pykF, metJ and purU.

In a preferred embodiment of the invention, the microorganism overexpresses the genes cysP, cysU, cysW, cysA, cysM, cysJ, cysI, cysH, cysE gcvT, gcvH, gcvP, metF metA (with reduced feed-back sensitivity), thrA (preferentially with reduced feed-back sensitivity) and metH., serA, serB, serC, glyA and represses the genes pykA, pykF, metJ and purU.

The man skilled in the art will know that other genes may require modifications to optimize methionine production. These genes have been identified particularly in WO2007/077041 and in WO2007/020295, incorporated herein by reference.

Culture Medium

In the method of the invention the modified microorganism is cultured in an appropriate culture medium comprising a source of carbon and a source of sulfur. An 'appropriate culture medium' is a medium appropriate for the culture and growth of the microorganism. Such mediums are well known to the person skilled in the art in microorganism fermentation, depending upon the microorganism being cultured.

The term 'carbon source' according to the present invention denotes any source of carbon that can be used by those skilled in the art to support the normal growth of a microorganism, which can be hexoses (such as glucose, galactose or lactose), pentoses, monosaccharides, disaccharides, oligosaccharides (such as sucrose, cellobiose or maltose), molasses, starch or its derivatives, hemicelluloses, glycerol and combinations thereof. An especially preferred simple carbon source is glucose. Another preferred simple carbon source is sucrose.

The sulphur source used for the fermentative production of L-methionine may be any of the following: sulfate, thiosulfate, hydrogen sulfide, dithionate, dithionite, sulfite, methylmercaptan, dimethyldisulfide or a combination thereof.

In a preferred embodiment of the invention, the sulphur source is sulfate and/or thiosulfate.

The nitrogen source may be an ammonium salt or ammoniac gas.

Improved Production of Methionine

In the invention, the methionine/carbon source yield is increased by enhancing the expression of the genes coding for succinate dehydrogenase. The term "methionine/carbon source yield" defines the quantity of methionine obtained during the fermentation divided by the quantity of the carbon source that has been consumed. It can be expressed in percent g methionine/g carbon source or mol methionine/mol carbon source. The term "enhanced" in this context describes a measurable increase compared to the microorganism without the specified modifications and/or the culture medium without the modifications. In preferred embodiments, the increase is of at least 1% g/g, preferably of at least 2% g/g. more preferably 4%.

To measure this increase the amount of consumed glucose and produced methionine has to be determined. The quantity of the carbon source that has been consumed is calculated by determining the glucose concentration in the growth medium by refractrometric HPLC or according to the method of Brix for fed-batch solutions. For batch cultures the consumed glucose corresponds to the amount of residual glucose at the beginning of the experiment from which the amount of the residual glucose at the end of the experiment is subtracted. For fed batch fermentation the amount of consumed glucose corresponds to the sum of glucose in the batch culture, the added glucose in the inoculum and the amount of glucose injected during the fed batch phase from which the amount of residual glucose at the end of the experiment is subtracted.

The term "methionine obtained" includes L-methionine and the easily recoverable methionine derivative NAM. The quantity of methionine obtained in the medium is measured by HPLC after OPA/Fmoc derivatization using L-methionine (Fluka, Ref 64319) as a standard. The amount of NAM is determined using refractometric HPLC using NAM (Sigma, Ref 01310) as a standard.

Methionine Recovery

After fermentation L-methionine, its precursors or compounds derived thereof such as N-acetyl-methionine are recovered and eventually purified. The methods for recovering and purifying the produced compounds are well-know to the skilled person. (WO 2005/007862, WO 2005/059155).

Example 1

MG1655 metA*11 Ptrc-metH PtrcF-cysPUWAM PtrcF-cysJIH Ptrc09-gcvTHP Ptrc36-ARNmst17-metF DmetJ DpykF DpykA DpurU (pME101-thrA*1-cysE-PgapA-metA*11) (pCC1BAC-sdh-CDAB-TT02-serB-glyA-serA-serC) and MG1655 metA*11 Ptrc-metH PtrcF-cysPUWAM PtrcF-cysJIH Ptrc09-gcvTHP Ptrc36-ARNmst17-metF DmetJ DpykF DpykA DpurU (pME101-thrA*1-cysE-PgapA-metA*11) (pCC1BAC-serB-glyA-serA-serC)

Methionine producing strains have been described in the patent application WO2009043803, WO2007/077041 and PCT/FR2009/052520 which are incorporated by reference.

1. Construction of the Vector pCC1BAC-sdhCDAB-TT02-serB-glyA-serA-serC

To increase the level of succinate deshydrogenase, SdhCDAB, in the methionine producing strain, the four genes sdhCDAB where cloned with their own promoter in the copy control vector pCC1BAC-serB-glyA-serA-serC (with the pCC1BAC vector from Epicentre) previously described in the patent application WO2009043803).

For this purpose, the sdhCDAB-TT02 region was amplified from the MG1655 E. coli genome using the oligonucleotides sdhCDAB-F and sdhCDAB-TT02-R (reference sequence on the website ecogene dot org/), with TT02 which is the T1 transcriptional terminator of the rrnB gene of E. coli (Orosz et al., 1991, Eur. J. Biochem. 201, 653). The resulting PCR product was cloned in the pSCB vector (Stratagene), verified by sequencing and the vector named pSCB-sdhCDAB-TT02.

(SEQ ID NO: 1)
sdhCDAB-F
atgcgt<u>GCATGC</u>atct<u>GGCGCC</u>GAATTGGTCAATACTTCCACACTGTTAC with
   a region (lower case) with extra-bases,
   a region (upper underlined case) harbouring SphI and SfoI site,
     a region (upper bold case) homologous to the sdhCDAB region (from 753931 to 753958)

(SEQ ID NO: 2)
sdhCDAB-TT02-R
aagcgct<u>GCATGC</u>AACAGATAAAACGAAAGGCCCAGTCTTTCGACTGAGC
*CTTTCGTTTTATTTGATG*TTTACGCATTACGTTGCAACAACATCG with
   a region (lower case) with extra-bases,
   a region (upper underlined case) harbouring SphI site,
   a region (upper italic case) for TT02 sequence which corresponds to the $T_1$ transcriptional terminator sequence of the rrnB gene of E. coli,
   a region (upper bold case) homologous to the sdhCDAB region (from 757603 to 757629).

To transfer the genes sdhCDAB-TT02 in the vector pCC1BAC, the vector pSCB-sdhCDAB-TT02 was restricted with the enzyme SphI and the sdhCDAB-TT02 region was cloned into the vector pCC1BAC-serB-glyA-serA-serC restricted by the same enzyme. The resulting vector was named pCC1BAC-sdhCDAB-TT02-serB-glyA-serA-serC.

2. Construction of the Strain MG1655 metA*11 Ptrc-metH PtrcF-cysPUWAM PtrcF-cysJIH Ptrc09-gcvTHP Ptrc36-ARNmst17-metF ΔmetJ ΔpykF DpykA ΔpurU (pME101-thrA*1-cysE-PgapA-metA*11) (pCC1BAC-sdhCDAB-TT02-serB-glyA-serA-serC)

Subsequently, the plasmids pME101-thrA*1-cysE-PgapA-metA*11 (previously described in the patent applications WO2007/077041 and PCT/FR2009/052520) and pCC1BAC-sdhCDAB-TT02-serB-glyA-serA-serC were introduced by electroporation into the strain MG1655 metA*11 Ptrc-metH PtrcF-cysPUWAM PtrcF-cysJIH Ptrc09-gcvTHP Ptrc36-ARNmst17-metF ΔmetJ ΔpykF DpykA ΔpurU giving the strain MG1655 metA*11 Ptrc-metH PtrcF-cysPUWAM PtrcF-cysJIH Ptrc09-gcvTHP Ptrc36-ARNmst17-metF ΔmetJ ΔpykF DpykA ΔpurU (pME101-thrA*1-cysE-PgapA-metA*11) (pCC1BAC-sdh-CDAB-TT02-serB-glyA-serA-serC).

3. Construction of the Strain MG1655 metA*11 Ptrc-metH PtrcF-cysPUWAM PtrcF-cysJIH Ptrc09-gcvTHP Ptrc36-ARNmst17-metF ΔmetJ ΔpykF DpykA ΔpurU (pME101-thrA*1-cysE-PgapA-metA*11) (pCC1BAC-serB-glyA-serA-serC)

The plasmids pME101-thrA*1-cysE-PgapA-metA*11 (previously described in the patent applications WO2007/077041 and PCT/FR2009/052520) and pCC1BAC-serB-glyA-serA-serC (previously described in the patent application WO2009043803) were introduced by electroporation into the strain MG1655 metA*11 Ptrc-metH PtrcF-cysPUWAM PtrcF-cysJIH Ptrc09-gcvTHP Ptrc36-ARNmst17-metF ΔmetJ ΔpykF DpykA ΔpurU giving the strain MG1655 metA*11 Ptrc-metH PtrcF-cysPUWAM PtrcF-cysJIH Ptrc09-gcvTHP Ptrc36-ARNmst17-metF ΔmetJ ΔpykF DpykA ΔpurU (pME101-thrA*1-cysE-PgapA-metA*11) (pCC1BAC-serB-glyA-serA-serC).

Example 2

Evaluation of the Strains

Strain 1: MG1655 metA*11 Ptrc-metH PtrcF-cysPUWAM PtrcF-cysJIH Ptrc09-gcvTHP Ptrc36-ARNmst17-metF DmetJ DpykF DpykA DpurU (pME101-thrA*1-cysE-PgapA-metA*11) (pCC1BAC-sdhCDAB-TT02-serB-TT07-glyA-serA-serC).

Strain 2: MG1655 metA*11 Ptrc-metH PtrcF-cysPUWAM PtrcF-cysJIH Ptrc09-gcvTHP Ptrc36-ARNmst17-metF DmetJ DpykF DpykA DpurU (pME101-thrA*1-cysE-PgapA-metA*11) (pCC1BAC-serB-glyA-serA-serC).

Production strains were evaluated in small Erlenmeyer flasks. A 5.5 mL preculture was grown at 37° C. for 16 hours in a mixed medium (10% LB medium (Sigma 25%) with 2.5 g·L$^{-1}$ glucose and 90% minimal medium PC1). It was used to inoculate a 50 mL culture to an OD$_{600}$ of 0.2 in medium PC1. If necessary spectinomycin and kanamycin were added to a final concentration of 50 mg·L$^{-1}$ and chloramphenicol to 30 mg·L$^{-1}$. The temperature of the cultures was 37° C. When the culture had reached an OD$_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation. For each strain, three repetitions were made.

TABLE 1

| Minimal medium composition (PC1). | |
|---|---|
| Compound | Concentration (g · L$^{-1}$) |
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |
| Citric acid | 6.00 |
| CaCl$_2$•2H$_2$O | 0.04 |
| K$_2$HPO$_4$•3H$_2$O | 10.50 |
| Na$_2$HPO$_4$ | 2.00 |
| (NH$_4$)$_2$HPO$_4$ | 8.00 |
| NH$_4$Cl | 0.13 |
| NaOH 4M | Adjusted to pH 6.8 |
| FeSO$_4$•7H$_2$O | 0.04 |
| Thiamine | 0.01 |
| Glucose | 10.00 |
| Ammonium thiosulfate | 5.60 |
| Vitamin B12 | 0.01 |
| MOPS | 10.00 |
| IPTG | 0.0024 |

TABLE 1

Methionine yield (Y$_{met}$) in % g methionine/g de glucose produced in batch culture by the different strains. For the exact definition of methionine/glucose yield see below.

| Strain | Y$_{met}$ | SD |
|---|---|---|
| Strain 1: (pCC1BAC-sdhCDAB-TT02-serB-TT07-glyA-serA-serC) | 12.85 | 0.24 |
| Strain 2: (pCC1BAC-serB-TT07-glyA-serA-serC) | 11.51 | 0.25 |

SD denotes the standard deviation for the yields which was calculated on the basis of three repetitions.

Extracellular methionine concentration was quantified by HPLC after OPA/FMOC derivatization. The residual glucose concentration was analyzed using HPLC with refractometric detection. The methionine yield was expressed as followed:

$$Y_{met} = \frac{\text{methionine (g)}}{\text{consummed glucose (g)}} * 100$$

As can be seen in table 1 the methionine/glucose yield (Ymet) is increased upon overexpression of sdhCDAB.

REFERENCES

1. Yankovskaya V, Horsefield R, Törnroth S, Luna-Chavez C, Miyoshi H, Léger C, Byrne B, Cecchini G, Iwata S, 2003, Science, 299, 700-704
2. Cheng V W, Johnson A, Rothery R A, Weiner J H, 2008, Biochemistry, 47, 9107-9116
3. Bussmann M, Emer D, Hasenbein S, Degraf S, Eikmanns B J, Bott M, 2009, J. Biotechnol, 143(3), 173-182
4. Dickson R C, Abelson J, Barnes W M, Reznikoff W S, 1975, 187(4171), 27-35
5. Brosius J, Erfle M, Storella J, 1985, J Biol Chem 260(6), 3539-41
6. Ptashne M, 1986; A genetic switch. Blackwell Scientific, Cambridge, Mass.
7. Ptashne M, 2004; A genetic switch: Phage lambda revisited. Cold Spring Harbor Lab Press. Cold Spring Harbor, N.Y.
8. Little J, 2004; The bacteriophages, Part II: Life of phages, 8. Gene regulatory circuitry of phage λ. 2nd edition 2004. Richard Calendar.ed. Oxford University Press
9. Carrier and Keasling, 1998, Biotechnol. Prog, 15, 58-64
10. Orosz A., Boras I., Venetianer P, 1991, European Journal of Biochemistry, 201, 653-659

The invention claimed is:

1. A method for the production of methionine, in a fermentative process comprising:
   (a) culturing a microorganism modified for an improved production of methionine in an appropriate culture medium comprising a source of carbon and a source of sulfur, and
   (b) recovering methionine from the culture medium, wherein said microorganism presents at least one of the following modifications:
   overexpression of the genes cysP, cysU, cysW, cysA, cysM, cysJ, cysI, cysH, cysE gcvT, gcvH, gcvP, metF, metA, thrA, metH, serA, serB, serC, glyA, and/or attenuation of the genes pykA, pykF, metJ, and purU, and wherein said microorganism is further modified by enhancing the expression of gene(s) encoding a succinate dehydrogenase enzyme by inserting into the microorganism at least one supplementary copy of the four genes sdhA, sdhB, sdhC, and sdhD of *E. coli*.

2. The method of claim 1, wherein said source of sulfur in the culture medium is sulfate, thiosulfate, hydrogen sulfide, dithionate, dithionite, sulfite or a combination thereof.

3. The method of claim 1, wherein said source of carbon is glucose or sucrose.

4. The method of claim 1, wherein said recovering methionine step comprises a step of isolating methionine from said culture medium.

5. The method of claim 1, wherein said microorganism is selected from the group consisting of a bacterium, yeast and fungus.

6. The method of claim 5, wherein said microorganism is a bacterium selected from the group consisting of Enterobacteriaceae and Coryneform bacteria.

7. The method of claim 5, wherein said microorganism is a bacterium selected from the group consisting of *E. coli* and *C. glutamicum*.

8. The method of claim 1, wherein said overexpression of the gene metA is overexpression of metA alleles which encode a homoserine succinyltransferase with reduced feed-back sensitivity to S-adenosylmethionine and/or methionine.

9. The method of claim 1, wherein said overexpression of the gene thrA is overexpression of thrA alleles which encode aspartokinases/homoserine dehydrogenase with reduced feed-back inhibition to threonine.

* * * * *

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Oligonucleotide sdhCDAB-F

<400> SEQUENCE: 1

```
atgcgtgcat gcatctggcg ccgaattggt caatacttcc acactgttac          50
```

<210> SEQ ID NO 2
<211> LENGTH: 95
<212> TYPE: DNA
<213> ORGANISM: Artificial Sequence
<220> FEATURE:
<223> OTHER INFORMATION: Oligonucleotide sdhCDAB-TT02-R

<400> SEQUENCE: 2

```
aagcgctgca tgcaacagat aaaacgaaag gcccagtctt tcgactgagc ctttcgtttt    60
atttgatgtt tacgcattac gttgcaacaa catcg                              95
```